United States Patent [19]

Maassen et al.

[11] 3,941,769

[45] Mar. 2, 1976

[54] PROCESS FOR THE PREPARATION OF SACCHAROSE-HYDROXY ALKYL ETHERS

[75] Inventors: Dieter Maassen; Roland Nast; Heinrich Bormann, all of Dormagen; Helmut Piechota, Leverkusen, all of Germany; Karl-Josef Kraft, Cora Opolis, Pa.

[73] Assignee: Bayer Aktiengesellschaft, Leverkusen, Germany

[22] Filed: Aug. 9, 1973

[21] Appl. No.: 387,067

[30] Foreign Application Priority Data
Aug. 22, 1972 Germany............................ 2241242

[52] U.S. Cl. ...... 260/209 R; 260/2.5 R; 260/2.5 AJ; 260/2.5 A; 260/210 R
[51] Int. Cl.² ........................................ C07H 15/08
[58] Field of Search ................................ 260/209 R

[56] References Cited
UNITED STATES PATENTS

| 3,085,085 | 4/1963 | Wismer et al. | 260/209 R |
| 3,153,002 | 10/1964 | Wismer et al. | 260/209 R |
| 3,169,934 | 2/1965 | Dennett et al. | 260/209 R |
| 3,326,890 | 6/1967 | Engelskirchen et al. | 260/209 R |
| 3,391,196 | 7/1968 | Earing et al. | 260/209 R |
| 3,433,751 | 3/1969 | Yatsuzuka et al. | 260/209 R |
| 3,441,616 | 4/1969 | Pizzini et al. | 260/209 R |
| 3,640,997 | 2/1972 | Fijal | 260/209 R |
| 3,829,412 | 8/1974 | Kunz | 260/209 R |

Primary Examiner—Johnnie R. Brown
Attorney, Agent, or Firm—Lawrence S. Pope; Gene Harsh

[57] ABSTRACT

A process for the preparation of saccharose polyethers which makes saccharose polyethers with a high functionality easily available. This is accomplished by subjecting mixtures of saccharose, a small quantity of water, a small quantity of a low molecular weight polyol, monoamine or polyamine or any combination of these to an alkoxylation reaction the reaction being carried out in suspension in aromatic hydrocarbon solvents and in the presence of alkali metal hydroxide catalysts.

8 Claims, No Drawings

PROCESS FOR THE PREPARATION OF SACCHAROSE-HYDROXY ALKYL ETHERS

This invention relates to a process for the preparation of polyalkylene glycol ethers based on saccharose which are valuable starting materials for the production of hard polyurethane foams.

It is known to react saccharose with alkylene oxides to produce saccharose-hydroxyalkyl ethers. Saccharose reacts with ethylene oxide in aqueous solution in the presence of sodium hydroxide (J. W. LeMaistre, R. B. Seymour, J. Org. Chem. 13, 782 (1948). A process for the preparation of saccharose-hydroxyalkyl ethers is based on this reaction in which saccharose is reacted with ethylene oxide or propylene oxide in concentrated aqueous solution at elevated temperature in the presence of potassium hydroxide as catalyst (U.S. Pat. Nos. 3,085,085 and 3,153,002, German Pat. No. 1,443,026).

The reaction of saccharose with alkylene oxides in aqueous solution is liable to be accompanied by unwanted side reactions, for example the partial hydrolysis of alkylene oxide by the water which is used as a reaction medium. The hydrolyzed alkylene oxide, the polyalkylene glycols formed from them as well as other by-products (indicated by a dark discoloration of the reaction mixture) have a deleterious effect on the properties of polyurethane foams produced from such saccharosehydroxyalkyl ethers. The high proportion of bifunctional linear by-products causes the functionality of these polyethers to be severly reduced compared with that of a pure saccharose polyol. The high proportion of bifunctional linear by-products present means that the saccharose polyethers produced by this method are only of limited use for the production of valuable polyurethane foams. This is because the use of such saccharose polyethers is likely to result in friable foams of moderate strength and non-uniform cell structure. Another disadvantage of polyurethane foams obtained from saccharose polyethers which have been prepared in this way is their low proportion of closed cells which causes them to be poor thermal insulators.

For this reason an attempt has already been made to carry out the alkoxylation of saccharose in the absence of water and in the presence of xylene (U.S. Pat. No. 2,652,394). This process, however, results in badly discolored products due to caramelization or charring of the saccharose.

The formation of high proportions of bifunctional by-products can be reduced by using a process in which saccharose is first reacted with 4 to 8 mols of alkylene oxide in a concentrated aqueous solution in the presence of potassium hydroxide. After this nearly all the water is removed from the reaction mixture and the addition of alkylene oxide is then continued (U.S. Pat. No. 3,085,085). Even in this process a high proportion of the alkylene oxide undergoes reaction in the presence of relatively large quantities of water in the reaction mixture. Hence even the products of this process tend to have the disadvantages described above which occur when the alkoxylation is carried out without an intermediate stage in which water is removed. One important technical difficulty of the known process of reacting saccharose with alkylene oxides in aqueous solution is that the major portion of sugar must be added at temperatures which are at or only slightly below the boiling point of water. Another disadvantage of this process is that the reaction velocity of alkylene oxide addition is relatively low, which greatly favors the formation of by-products during the alkylene oxide addition reaction.

It is also known that saccharose, present in a suspension in glycerol, can be reacted with propylene oxide in the presence of potassium hydroxide and a small quantity of water, a polyether mixture being obtained which in addition to propoxylated saccharose contains a high proportion of propoxylated glycerol (U.S. Pat. No. 3,442,888). The polyethers prepared by this process still contain a substantial proportion of linear polypropylene glycols in addition to the propoxylated saccharose and propoxylated glycerol, due to the reaction of propylene oxide with the water present in the reaction mixture. This, and particularly the high proportion of glycerol polyethers, causes the functionality of polyethers obtained by this process to be much lower than the functionality of a pure saccharose polyol. This low functionality has an undesirable effect on the properties of polyurethane foams produced from such saccharose-glycerol polyols.

It is essential when reacting saccharose with alkylene oxides that the reaction mixture be freely stirrable. Adequate removal of the large amount of heat produced in the reaction with alkylene oxides is only possible if the reaction mixture can be stirred vigorously. The problem of being able to stir the mixture is particularly difficult when the saccharose is first introduced and when large quantities of unreacted solid saccharose are present during the addition of alkylene oxide. Mixtures of saccharose and alkali metal hydroxide which are difficult to stir may lead to caramelization or charring reactions on the walls of the reaction vessel which are inevitably hot due to the heating of the reaction mixture.

Previously one could only insure that the reaction mixtures which contain saccharose would be freely stirrable by using fairly concentrated solutions of saccharose in water or by suspending saccharose in a large quantity of glycerol. These methods have serious disadvantages, as already described above. The possibilities of reducing the extent of the side reactions by reducing the water content of aqueous solutions or of suspensions are limited since mixtures of saccharose and potassium hydroxide which contain less than 5% of water cannot be easily stirred.

It is therefore an object of this invention to provide a process for the preparation of saccharose polyethers which makes saccharose polyethers with a high functionality easily available and substantially eliminates the disadvantages of the existing processes as described above.

According to the invention, this problem has been solved by subjecting mixtures of saccharose, a small quantity of water, a small quantity of a low molecular weight polyol, monoamine or polyamine or any combination of these to an alkoxylation reaction the reaction being carried out in suspension in aromatic hydrocarbon solvents and in the presence of alkali metal hydroxide catalysts.

This invention therefore relates to a process for the preparation of saccharose-hydroxyalkyl ethers by the alkoxylation of saccharose, characterized in that a mixture containing a. 100 parts by weight saccharose,
b. 2 – 5 parts by weight of water, c. 2 - 20 parts by weight of a low molecular weight higher valent alcohol, monoamine or polyamine or any combination of these, d. 40 – 150 parts by weight of an aromatic hydrocarbon solvent and e. 1 – 5 parts by weight of an alkali metal hydroxide is first prepared at temperatures of between 20°C and 110°C, and the mixture is then reacted with alkylene oxides at temperatures of 85° to 130°C and pressures of 1.3 to 5.0 atmospheres.

The process according to the invention is preferably carried out as follows:

Saccharose is first suspended at room temperature, normally between 10°C and 30°C in an aromatic hydrocarbon solvent, the quantity of solvent used being 40 to 150%, preferably 50 to 100% of the weight of saccharose.

A quantity of a water-soluble, short chained polyol, monoamine or polyamine which is small compared with the quantity of sugar, a small quantity of water and a small quantity of alkali metal hydroxide used as catalyst are added in any sequence to this suspension under an atmosphere of nitrogen at temperatures of between 20°C and 110°C preferably between 50°C and 90°C, the alkali metal hydroxide being preferably used in the form of a concentrated aqueous solution. The resulting mixture which is an easily stirrable paste is then heated to the reaction temperature of 85° to 130°C, preferably 95° to 115°C, and then reacted with alkylene oxide at pressure of 1.3 to 5.0 atmospheres, preferably 1.5 to 3.5 atmospheres. The reaction temperature is maintained within the range of 85° to 130°C, preferably 95° to 115°C, either by heating or by cooling of the reaction mixture, as required. When alkyleneoxide addition has been completed the alkaline polymer is neutralized with dilute mineral acid. If desired, an anti-oxidant, e.g. 2,6-di-tert. butyl-p-cresol, may be added to the neutralized product. The water and hydrocarbon are distilled off down to a small residue under vacuum at elevated temperatures, about 50° to 130°C, and the salts which separate in the process are removed by filtration.

Any aromatic hydrocarbon solvents boiling within the range of 80° to 180°C may be used for the process of the invention, for example benzene, toluene, ethyl benzene, xylenes or chlorobenzene. The preferred solvent for the process of the invention is toluene. The aromatic hydrocarbons may also be used as mixtures with aliphatic solvents boiling within the range of 80° to 180°C.

The polyols, monoamine and/or polyamines used for the process according to the invention are water-soluble compounds which have melting points below 100°C and molecular weights generally between 60 to 250. Examples of such compounds are: ethylene glycol, propylene glycol, butane-1,4-diol, diethylene glycol, dipropylene glycol, trimethylol propane, glycerol, sorbitol, mannitol, mono-, di- and triethanolamine, mono-, di and triisopropanolamine, N-alkyl-alkanolamines such as N-methyl-diethanolamine and N-ethyl-diethanolamine, lower aliphatic monoalkylamines and dialkylamines, cycloalkylamines, aralkylamines, alkylene diamines such as ethylene diamine and polyalkylene polyamines such as diethylene triamine and triethylene tetramine. The preferred compounds for the process of the invention are higher valent alcohols and amino alcohols.

Instead of the pure compounds there may also be used mixtures of two or more of the additives described above. In either case, the total quantity of additives used is 2 to 20%, preferably 3 to 15% of the weight of saccharose.

According to the invention, the water content of the mixture of saccharose, additives and catalyst is between 1 and 5%, preferably between 2.0 and 4.5% of the weight of the saccharose portion.

The reaction with the alkylene oxide is carried out in the presence of alkali metal hydroxides as catalyst, preferably sodium hydroxide or potassium hydroxide. According to a preferred method of carrying out the process, potassium hydroxide is used in the form of an approximately 50% aqueous solution and the quantity of potassium hydroxide used is between 1.0 and 5.0%, preferably between 2.0 and 3.0% of the weight of saccharose.

The alkylene oxides used in the process according to the invention are preferably ethylene oxide, propylene oxide and/or 1,2-butylene oxide. The alkoxylation reaction according to the invention may be carried out using either only one of the above mentioned alkylene oxides or any mixtures of alkylene oxides. If desired, various alkylene oxides may be added in succession to a reaction mixture in the process according to the invention to produce so-called graft polyethers.

The reaction temperatures may vary within a wide range. Temperatures of between 85° and 130°C and preferably between 95° and 115°C are generally employed. The reaction with alkylene oxides is carried out at an elevated pressure of between 1.3 and 5.0 atmospheres, preferably between 1.5 and 3.5 atmospheres.

The process according to the invention may be applied to the preparation of polyethers which can be reacted with polyisocyanates to produce hard polyurethane foams. These foams are either directly produced with polyisocyanates or only after they have been mixed with suitable short chain diols or polyols or bifunctional or polyfunctional polyalkylene glycols. When it is desired to make such hard foams the quantity of alkylene oxide used is such that each saccharose molecule reacts on an average with about 8 to 20 and preferably about 8 to 15 molecules of alkylene oxide. The polyethers obtained in this way have hydroxyl numbers of between 250 and 750, preferably between 350 and 550. The functionality of the polyethers is above 5.5 in the case of products with a low hydroxyl number and in the region of 7 or more in the case of products with a high hydroxyl number.

The polyethers prepared in accordance with the invention are clear, yellowish to brownish, thick liquid or highly viscous oils. The viscosity of the products depends on the hydroxyl number and quantity of additives contained in them and varies from 7000 cP (at 25°C) in the case of low hydroxyl numbers (about 350) to above 400,000 cP in the case of high hydroxyl numbers (about 550). By varying the hydroxyl number and the proportion of additives rather than by varying the small water content it is possible to produce products whose viscosity is optimally adjusted in each case to the given use purpose of the product.

The following are the major advantages of the process according to the invention:

The saccharose can be introduced at room temperature, normally between 10 and 30°C, so that trouble caused by solvent vapors or hot steam can easily be avoided.

The inert atmosphere which is absolutely essential for the reaction with alkylene oxides can very easily be achieved since at room temperature atmospheric oxygen can easily be removed by repeated evacuation of the reaction vessel and refilling with nitrogen.

The mixtures of starting materials are easily stirrable at every phase of the reaction. This ensures efficient cooling which is necessary for rapid reaction with alkylene oxides.

The reaction mixtures are characterized by a relatively high reaction velocity in the reaction with alkylene oxides.

Due to the ease with which the system can be stirred, saccharose is prevented from caking on the hot walls of the reaction vessel and carmelization of saccharose is therefore avoided.

The saccharose undergoes complete reaction with alkylene oxides without any residue. Due to the small water content of the reaction mixtures, side reactions of alkylene oxides occur only to a slight extent.

The saccharose polyethers prepared by the process according to the invention are pale in color and due to the relatively high proportion of saccharose-hydroxyalkyl ethers in them they have a relatively high functionality.

The process according to the invention may, of course, also be modified so that only part of the alkylene oxide is reacted at first and the remainder is added only after an intermediate removal of water.

The saccharose polyethers obtained by the process according to the invention are valuable starting materials for the production of hard polyurethane foams by known processes for the production of polyurethane foams by reaction with preferably aromatic polyisocyanates in the presence of the usual auxiliary agents and additives.

The apparatus used for carrying out the practical examples described below was an autoclave equipped with a heating and cooling device, a stirrer, a device for displacing air with gaseous nitrogen (e.g. vacuum attachment and nitrogen inlet) and a device for adding alkylene oxide.

The invention is further illustrated but is not intended to be limited by the following examples in which all parts and percentages are by weight unless otherwise specified.

EXAMPLE 1

350 kg of saccharose (1025 mol) were introduced into 182 kg of toluene at room temperature with stirring. Atmospheric oxygen was removed from the reaction vessel by twice evacuating the vessel and refilling with nitrogen. The easily stirrable suspension of saccharose in toluene was heated and 20 kg of 1,2-propylene glycol, 15.0 kg of 50% aqueous potassium hydroxide solution and 5.9 kg of water were added successively at 80°C (total quantity of water together with the water used for dissolving the potassium hydroxide; 13.4 kg; 3.83% of water based on the quantity of saccharose). The easily stirrable, pasty mixture was heated to 105°C and 874 kg (15070 mol) of propylene oxide were gradually added at a pressure of 2.3 to 1.6 atmospheres and a temperature of 104° to 105°C (55 kg per hour; propylene oxide introduced under the surface of the reaction mixture). The reaction temperature was kept within this range by either cooling or heating the reaction mixture as required. Stirring was continued for a further 3 hours at 105°C after all the propylene oxide had been added.

After the addition of 250 kg of water, the alkaline polymer was neutralized with 51 kg of 12.6% aqueous sulphuric acid (pH of the emulsion 6.4). Water and toluene were then distilled off under vacuum at 70° to 90°C after the addition of filtering agents (cellulose powder and synthetic magnesium silicate) and an antioxidant (2,6-di-tert.-butyl-p-cresol). When the water content of the product was 0.9%, the salts which separated and the filtering agents were filtered off after the addition of 150 liters of toluene. The filtrate was then distilled under vacuum of 85° to 99°C for complete removal of water and toluene.

The resulting pale yellow, viscous product had the following physical properties:

| | |
|---|---|
| Hydroxyl number (mg KOH/g) | 416 |
| pH | 7.3 |
| Water content (%) | 0.05 |
| Viscosity $n_{25°}$ (cP) | 28000 |
| average functionality (calculated from the quantity of starting material and hydroxyl number) | 5.95 |

Remarks:

The hydroxyl numbers given in the examples were determined by the usual method of acylating the polyether with excess phthalic acid anhydride in pyridine.

To determine the pH values, a mixture of methanol and water in a volumetric ratio of 9 : 1 was used as solvent and 10 ml of the polyether and 100 ml of the solvent were used for the pH determination. The measurement was carried out using a single-rod glass electrode.

EXAMPLE 2

Introduction of the starting components, addition of alkylene oxide and working up of the alkaline polymer were carried out as described in Example 1.

The following starting materials were used:

| | |
|---|---|
| 165 | kg of toluene |
| 315 | kg (921 mol) of saccharose, |
| 32.7 | kg of trimethylol propane, |
| 9.2 | kg of propylene glycol, |
| 13.4 | kg |
| 5.6 | kg of water (total quantity of water 12.3 kg, 3.9% of water based on the weight of the saccharose) |
| 828 | kg (14280 mol) of propylene oxide in 15 hours. |

First saccharose was added at room temperature, followed by trimethylol propane at 60° to 70°C and then by propylene glycol, potassium hydroxide solution and water in that order at 80°C. The mixture of starting components was freely stirrable.

The pale yellow, viscous product obtained had the following physical properties:

| | |
|---|---|
| hydroxyl number (mg KOH/g) | 417 |
| pH | 7.3 |
| water content (%) | 0.08 |
| viscosity $n_{25°}$ (cP) | 21300 |
| average functionality (calculated from the quantity of starting material and hydroxyl number) | 5.75 |

EXAMPLE 3

The introduction of starting components, addition of alkylene oxide and working up of the alkaline polymer were carried out as described in Example 1.

The following starting materials were used:

182 kg of toluene
350 kg (1025 mol) of saccharose,
20 kg of propylene glycol,
15.0 kg of 50% aqueous potassium hydroxide solution,
6.0 kg of water (total quantity of water 13.5 kg; 3.85% based on the weight of saccharose),
696 kg (12010 mol) of propylene oxide in 13.5 hours.

Saccharose was first added at room temperature and then, at 80°C, propylene glycol, potassium hydroxide and water in that order. The mixture of starting components was freely stirrable.

The pale yellow, viscous product obtained had the following physical properties:

| | |
|---|---|
| hydroxyl number (mg KOH/g) | 470 |
| pH | 7.3 |
| water content (%) | 0.08 |
| viscosity $n_{25°}$ (cP) | 104000 |
| average functionality (calculated from quantity of starting material and hydroxyl number) | 6.30 |

EXAMPLE 4

The introduction of starting components, addition of alkylene oxide and working up of the alkaline polymer were carried out as described in Example 1. The components were introduced in the following sequence:
1,330 g of toluene
2,670 g (7.81 mol) of saccharose at about 25°C,
91.5 g of propylene glycol at 80°C,
73.5 g of water at 80°C,
110.0 g of 50% aqueous potassium hydroxide solution at 80°C (total quantity of water 128.5 g; 4.8% of water based on the weight of saccharose),
4,239 g of propylene oxide (73.0 mol) in 14 hours.

The addition of propylene oxide was carried out at 1.4 to 1.6 atmospheres.

The mixture of starting components was freely stirrable.

The brownish yellow, highly viscous product obtained had the following physical properties:

| | |
|---|---|
| hydroxyl number (mg KOH/g) (the hydroxyl number was determined with acetic acid anhydride in pyridine) | 519 |
| pH | 6.6 |
| water content (%) | 0.05 |
| viscosity $n_{25°}$ (cP) | 400,000 |
| average functionality (calculated from the quantity of starting material and hydroxyl number) | 7.18 |

EXAMPLE 5

The introduction of starting components, addition of alkylene oxide and working up of the alkaline polymer were carried out as described in Example 1. The starting components were introduced in the following sequence:
1,310 g of toluene
2,180 g (6.38 mol) of saccharose at about 25°C,
251 g of triethanolamine at 80°C
46 g of water at 80°C
104 g of 50% aqueous potassium hydroxide solution at 85°C (total quantity of water 98.0 g; 4.5% based on the weight of saccharose),
6,254 g (112.6 mol) of propylene oxide in 20 hours.

The addition of propylene oxide was carried out at 0.4 to 0.6 excess atmospheres.

The mixture of starting components was freely stirrable.

The brownish yellow, viscous product obtained had the following physical properties:

| | |
|---|---|
| hydroxyl number (mg KOH/g) | 376 |
| pH | 9.05 |
| water content (%) | 0.04 |
| viscosity $n_{25°}$ (cP) | 11780 |
| average functionality (based on the quantity of starting material and hydroxyl number) | 5.96 |

EXAMPLE 6

The introduction of starting components, addition of alkylene oxide and working up of the alkaline polymer were carried out as described in Example 1. The starting components were added in the following sequence:
125 kg of toluene
291 kg (850 mol) of saccharose at about 25°C,
30.0 kg of trimethylol propane at 70°C,
6.0 kg of water at 80°C,
18.5 kg of 50% aqueous potassium hydroxide solution at 80°C (total quantity of water 15.25 kg; 5.24% of water based on the weight of saccharose),
873 kg (15,080 mol) of propylene oxide in 16 hours.

The mixture of starting components was freely stirrable.

The brownish yellow viscous product obtained had the following physical properties:

| | |
|---|---|
| hydroxyl number (mg KOH/g) | 382 |
| pH | 6.9 |
| water content (%) | 0.09 |
| viscosity $n_{25°}$ (cP) | 13825 |
| average functionality (calculated from quantity of starting material and hydroxyl number) | 5.77 |

EXAMPLE 7

The introduction of starting components, addition of alkylene oxide and working up of the alkaline polymer were carried out as described in Example 1. The starting materials were introduced in the following sequence:
1,000 g of toluene
1,685 g (4.93 mol) of saccharose at about 25°C,
107 g of ethylene diamine at 80°C
46 g of water at 80°C,
70 g of 50% aqueous potassium hydroxide solution at 80°C (total quantity of water 81.0 g; 4.8% of water based on the weight of saccharose),
5,200 g (89.7 mol) of propylene oxide in 23 hours The addition of propylene oxide was carried out at 0.4 to 0.6 excess atmosphere.

The mixture of starting components was freely stirrable.

The brownish yellow, viscous product obtained had the following physical properties:

| | |
|---|---|
| hydroxyl number (mg KOH/g) | 398 |
| pH | 10.3 |
| water content (%) | 0.159 |
| viscosity $n_{25°}$ (cP) | 16350 |
| average functionality (calculated from starting material and hydroxyl number) | 6.01 |

EXAMPLE 8

In this example there is described the preparation of a saccharose polyether which was prepared from a mixture of propylene oxide and ethylene oxide. The introduction of starting components, addition of alkylene oxides and working up of the alkaline polymer were carried out as described in Example 1.

The starting materials were introduced in the following sequence:

121 kg of toluene
286 kg (837 mol) of saccharose at about 25°C,
29.8 kg of trimethylol propane at 70° – 75°C,
8.4 kg of propylene glycol at 80° – 85°C,
5.4 kg of water at 85°C,
12.0 kg of 50% aqueous potassium hydroxide solution at 85°C (total quantity of water 11.4 kg; 3.98% of water based on the weight of saccharose),
652 kg (11230 mol) of propylene oxide,
218 kg (4960 mol) of ethylene oxide as mixture in 13 hours.

The mixture of starting components was freely stirrable.

The pale yellow, viscous product obtained had the following physical properties:

| | |
|---|---|
| hydroxyl number (mg KOH/g) | 374 |
| pH | 7.4 |
| water content (%) | 0.09 |
| viscosity n₂₅₀ (cP) | 7500 |
| average functionality (calculated from starting material and hydroxyl number) | 5.83 |

EXAMPLE 9

In this example there is described a saccharose polyether which was prepared by first adding propylene oxide and then adding ethylene oxide only after all the propylene oxide had been added and the reaction has been left to continue for 2 hours after the addition of propylene oxide. The introduction of starting components, addition of alkylene oxides (the pressure in the reaction vessel was increased to 2 excess atmospheres during the addition of ethylene oxide) and working up of the alkaline polymer were carried out as described in Example 1. The starting materials were introduced in the following sequence:

156 kg of toluene
302 kg (883 mol) of saccharose at about 25°C,
18.1 kg of trimethylol propane at 70° – 75°C,
8.5 kg of propylene glycol at 80°C,
5.0 kg of water at 80°C,
12.0 kg of 50% aqueous potassium hydroxide solution at 80° – 85°C (total quantity of water 11.0 kg; 3.64% of water based on the weight of saccharose),
819 kg (14120 mol) of propylene oxide in 15 hours
48 kg (1091 mol) of ethylene oxide in 1.2 hours.

The mixture of starting components was freely stirrable. The brownish yellow, viscous product obtained had the following physical properties:

| | |
|---|---|
| hydroxyl number (mg KOH/g) | 382 |
| pH | 7.6 |
| water content (%) | 0.05 |
| viscosity n₂₅₀ (cP) | 13600 |
| average functionality (calculated on starting material and hydroxyl number) | 6.00 |

COMPARISON EXAMPLE

The stirrability of a mixture of 30.0 g of 50% aqueous potassium hydroxide solution, 11.3 g of water and 500.0 g of saccharose (total quantity of water 26.3 g; 5.26% of water based on the weight of saccharose) was tested in a two liter hard glass beaker fitted with lid and blade stirrer with glass shaft.

Aqueous potassium hydroxide solution and water were introduced into the beaker. About 100 g of saccharose were first introduced at about 50°C with stirring. Additional saccharose was gradually stirred in at 90° – 95°C. The thick, pasty mixture obtained after the addition of a total of 440 g of saccharose was still stirrable. By the time 500 g of saccharose had been added, the mixture was very tough and no longer stirrable, there was a marked formation of lumps and the stirrer broke after a few minutes.

It is to be understood that any of the components and conditions mentioned as suitable herein can be substituted for its counterpart in the foregoing examples and that although the invention has been described in considerable detail in the foregoing, such detail is solely for the purpose of illustration. Variations can be made in the invention by those skilled in the art without departing from the spirit and scope of the invention except as is set forth in the claims.

What is claimed is:

1. In a process for the preparation of saccharose-hydroxyalkyl ethers by the alkoxylation of saccharose with alkylene oxides selected from the group consisting of ethylene oxide, propylene oxide and 1,2-butylene oxide at a temperature of 85° to 130°C and a pressure of 1.3 to 5.0 atmospheres the improvement comprising reacting the alkylene oxides with a mixture containing
   a. 100 parts by weight of saccharose,
   b. 2–5 parts by weight of water,
   c. 3–15 parts by weight of a low molecular weight higher valent alcohol, momoamine, or polyamine or any mixture of these wherein the alcohol, monoamine, or polyamine is water soluble, has a melting point below 100°C and a molecular weight of between 60 and 250,
   d. 40–150 parts by weight of an aromatic hydrocarbon solvent, and
   e. 1–5 parts by weight of an alkali metal hydroxide, wherein said mixture is initially prepared at temperatures of between 20° and 100°C.

2. A process according to claim 1 wherein the aromatic hydrocarbon solvents used are benzene, toluene, ethyl benzene, xylenes or chlorobenzene.

3. A process according to claim 1 wherein the alkali metal hydroxide used is 2.0 to 3.0 parts by weight of potassium hydroxide in the form of a concentrated aqueous solution.

4. A process according to claim 1 wherein the alcohol, monoamine or polyamine is water soluble.

5. A process according to claim 1 wherein the amount of alcohol, monoamines or polyamines used is present in a quantity of 2 – 20 percent by weight, based on the saccharose.

6. A process according to claim 1 wherein the alkylene oxide is a mixture of ethylene oxide and/or propylene oxide and/or 1,2-butylene oxide.

7. A process according to claim 1 wherein the alkylene oxide is selected from at least two members of the group consisting of ethylene oxide, propylene oxide and 1,2-butylene oxide and wherein the alkylene oxides are added in succession to the reaction mixture to produce graft polyethers.

8. A process according to claim 1 wherein the alkylene oxide is used in a quantity which corresponds to a molar ratio of saccharose : alkylene oxide as 1 : 8 to 1 : 20.

* * * * *